United States Patent [19]
Ladd

[11] Patent Number: 5,958,372
[45] Date of Patent: Sep. 28, 1999

[54] LOW VISCOSITY CHELATING POLYMERS FOR DIAGNOSTIC IMAGING

[75] Inventor: David L. Ladd, Wayne, Pa.

[73] Assignee: Nycomed Imaging AS, Norway

[21] Appl. No.: 08/266,835

[22] Filed: Jun. 28, 1994

[51] Int. Cl.[6] .................................................. A61B 5/055
[52] U.S. Cl. ......................... 424/1.65; 424/9.34; 534/16; 556/50; 556/55; 556/63; 556/77; 556/105; 556/116; 556/134; 556/148; 540/465; 514/182; 514/492; 514/836
[58] Field of Search .................................. 424/9.34, 1.65; 128/653.4, 654; 436/173; 514/836, 182, 492; 540/465; 534/16; 556/50, 55, 63, 77, 105, 116, 134, 148; 600/420

[56] References Cited

U.S. PATENT DOCUMENTS

| | | | |
|---|---|---|---|
| 5,057,313 | 10/1991 | Shih et al. | 424/85.91 |
| 5,230,883 | 7/1993 | Kornguth et al. | 424/9 |
| 5,252,317 | 10/1993 | Keana | 424/9 |
| 5,308,604 | 5/1994 | Sinn et al. | 424/9 |
| 5,324,503 | 6/1994 | Lin et al. | 424/5 |
| 5,330,743 | 7/1994 | Gibby et al. | 424/9 |
| 5,334,371 | 8/1994 | Gries et al. | 424/9 |
| 5,364,613 | 11/1994 | Sieving et al. | 424/9 |
| 5,364,614 | 11/1994 | Platzek et al. | 424/9 |

FOREIGN PATENT DOCUMENTS

| | | |
|---|---|---|
| 299 795 | 7/1987 | European Pat. Off. . |
| A 0 233 619 | 8/1987 | European Pat. Off. . |
| WO A 90 12050 | 10/1990 | WIPO . |
| WO A 92 00748 | 1/1992 | WIPO . |
| WO A 94 05203 | 3/1994 | WIPO . |
| WO A 94 08629 | 4/1994 | WIPO . |
| WO A 94 28940 | 12/1994 | WIPO . |

*Primary Examiner*—Gary E. Hollinden
*Attorney, Agent, or Firm*—Fish & Richardson P.C.

[57] ABSTRACT

Disclosed are linear and cross-linked polymers suitable for use as a contrast agent for magnetic resonance imaging containing units comprising the residue of a poly(amine) moiety linked to a chelating agent and to one or more pendant (poly)alkylene oxides.

12 Claims, 3 Drawing Sheets

LOW VISCOSITY CHELATING POLYMERS FOR DIAGNOSTIC IMAGING

FIELD OF INVENTION

This invention relates to chelating polymers useful as magnetic resonance (MR) contrast agents for use in MR imaging compositions and methods. More particularly, this invention relates to linear and cross-linked α-(polyamino)-ω-methoxypoly(alkyleneoxide)-DTPA polymers and their metal chelates.

BACKGROUND OF THE INVENTION

Magnetic resonance (MR) is widely used for obtaining spatial images of human subjects for clinical diagnosis. A review of this technology and clinical applications is provided by D. P. Swanson et al., in *Pharmaceuticals in Medical Imaging*, 1990, Macmillan Publishing Company, pages 645–681.

MR images are derived as a composite of the effects of a number of parameters which are analyzed and combined by computer. Choice of the appropriate instrument parameters, such as radio frequency (Rf), pulsing and timing can be utilized to enhance or attenuate the signals of any of the image-producing parameters thereby improving image quality and provide better anatomical and functional information. In many cases, MR imaging has proven to be a valuable diagnostic tool, inasmuch as normal and diseased tissue, by virtue of their possessing different parameter values, can be differentiated in the image.

In MR imaging, the in vivo image of an organ or tissue is obtained by placing the body of a subject in a strong external magnetic field, pulsing with radio frequency energy, and observing the effect of the pulses on the magnetic properties of the protons contained in and surrounding the organ or tissue. A number of parameters can be measured. The proton relaxation times, $T_1$ and $T_2$, are of primary importance. $T_1$, also called the spin-lattice or longitudinal relaxation time, and $T_2$, also called the spin-spin or transverse relaxation time, are functions of the chemical and physical environment of the organ or tissue water and are measured using Rf pulsing techniques. This information is analyzed as a function of spatial location by computer which transforms the information to generate an image.

Often the image produced lacks appropriate contrast, e.g., between normal and diseased tissue, reducing diagnostic effectiveness. To overcome this drawback, contrast agents have been used. Contrast agents are substances which exert an effect on the MR parameters of various chemical species proximal to them. Theoretically, a contrast agent, if taken up preferentially by a certain portion of an organ or a certain type of tissue, e.g., diseased tissue, can provide contrast enhancement in the resultant images.

Inasmuch as MR images are strongly affected by variations in the $T_1$ and $T_2$ parameters, it is desirable to have a contrast agent which affects either or both parameters. Research has focused predominantly on two classes of magnetically active materials, i.e., paramagnetic materials, which act primarily to decrease $T_1$, and superparamagnetic materials, which act primarily to decrease $T_2$.

Paramagnetism occurs in materials that contain unpaired electrons. Paramagnetic materials are characterized by a weak magnetic susceptibility (response to an applied magnetic field). Paramagnetic materials become weakly magnetic in the presence of a magnetic field and rapidly lose such activity, i.e., demagnetize, once the external field has been removed. It has long been recognized that the addition of paramagnetic solutes to water causes a decrease in the $T_1$ parameter.

Paramagnetic materials, for example, Gd containing materials, have been used as MR contrast agents primarily because of their effect on $T_1$. Gd has the largest number of unpaired electron (seven) in its 4f orbitals and exhibits the greatest longitudinal relaxivity of any element.

A major concern with the use of contrast agents for MR imaging is that many paramagnetic materials exert toxic effects on biological systems making them inappropriate for in vivo use. For example, the free solubilized form of Gd salts are quite toxic. To make the gadolinium ion more suitable for in vivo use, researchers have chelated it with diethylenetriaminepentaacetic acid (DTPA). A formulation of this material that has undergone extensive clinical testing consists of Gd-DTPA neutralized with two equivalents of N-methyl-D-glucamine (meglumine). This agent has been successful in enhancing human brain and renal tumors.

Despite its satisfactory relaxivity and safety, this formulation has several disadvantages. For example, due to its low molecular weight, Gd-DTPA dimeglumine is cleared very rapidly from the blood stream and tissue lesions (tumors). This limits the imaging window, the number of optimal images that can be taken after each injection, and increases the agents required dose and relative toxicity. In addition, the biodistribution of Gd-DTPA is suboptimal for imaging body tumors and infections due to its small molecular size.

Several approaches have been taken in attempts to overcome these disadvantages. For example, Gd and Gd-chelates have been chemically conjugated to macromolecular proteins such as albumin, polylysines and immunoglobulins. Drawbacks of conjugating DTPA to protein carriers for use in MR image enhancement include inappropriate biodistribution and toxicity. In addition, proteins provide a defined platform not subject to wide synthetic variation. Additionally, thermal sterilization of protein conjugates tends to be problematic, especially in the case of albumin conjugates.

To overcome these drawbacks, PCT/US93/09766 contacts a chelating agent with poly(alkylene oxide) to form a metallizable polymer which, when associated with paramagnetic metal ions, provide polymeric chelates with improved utility as contrast agents for MR imaging. For example, such polymeric chelates contain relatively large amounts of metal, are potentially more stable in vivo, and are less immunoreactive than protein-chelate-metal complexes.

However, incorporation of the poly(alkylene oxide) moiety into the backbone of the polymer contributes to increased viscosity of the polymeric composition, thereby limiting formulation concentration and raising injection volume in order to maintain acceptable formulation viscosity.

Thus, it is readily apparent that it would be highly desirable to provide other polymeric MR contrast agents which also contain relatively large amounts of metal per molecule, i.e., are of high substitution ratios; are of a molecular weight enabling them to be circulated within the blood pool for extended periods of time; exhibit improved biodistribution for imaging blood vessels, body tumors and other tissues; yet yield low viscosity contrast compositions that maximize injectable concentration and minimize injectable volume.

SUMMARY OF THE INVENTION

We have discovered that reactive α-(polyamino)poly (alkylene oxides) can be contacted with chelating agents or precursors thereof containing reactive functionality to form metallizeable graft co-polymers which, when associated with paramagnetic metal ions, provide polymeric chelates of extraordinary utility as contrast agents for MR imaging. Such polymers have a more globular shape when compared to linear co-polymers, resulting in decreased viscosity and increased relaxivity.

We have also found that the use of polyamine linking groups with three or more amine groups introduces the potential for cross-linking and results in a polymer with a more globular shape, thereby further decreasing viscosity and increasing relaxivity.

More particularly, in accordance with this invention, there is provided a polymer, suitable for use as a contrast agent for MR imaging, containing units comprising a chelating agent linked to the residue of a polyamine moiety, from which is subtended one or more pendant mono-functional polyalkylene oxides capped with H or alkoxy. The polymer, which may be linear or cross-linked, preferably comprises units having the structure I.

where
L and R"=the residue of a linking group such as a polyamine
R=H or an alkyl group such as $CH_3$
R'=H, alkyl, aralkyl or —PAO—OR
PAO=a polyalkyleneoxide of MW 100–20,000
metal=any paramagnetic or radioactive metal
chelator=DTPA, P4A, EDTA, etc.
y=0–10
x=2–1000

This invention further provides a method of performing an MR diagnostic procedure in a body comprising administering to the body a contrast enhancing amount of the polymer described above, and then exposing the body to an MR measurement step to image at least a portion of the body.

It is a particularly advantageous feature that the paramagnetic polymeric chelates of this invention provide effective MR contrast enhancement of the blood pool within the vascular system for remarkably long periods of time.

It is an advantageous feature of this invention that polymeric compounds are provided having a specificity toward accumulation in different tissues, for example, in tumors and the liver.

It is another advantageous feature of this invention that polymeric chelates suitable for MR imaging are provided containing relatively large amounts of metal that are potentially more stable in vivo and less immunoreactive than protein-chelate-metal complexes.

Yet another advantageous feature of this invention is that the molecular weight of the above-described polymers can be synthetically tailored to produce an agent of desired composition, molecular weight and size.

These agents also offer decreased viscosity, resulting from the non-linear shape of the polymer, and increased relaxivity.

Still other advantageous features of this invention will become readily apparent upon reference to the following description of preferred embodiments.

DESCRIPTION OF PREFERRED EMBODIMENTS

While the polymer of this invention is described herein primarily in connection with its preferred utilities, i.e., as a contrast agent for use in MR imaging compositions and methods, it also finds utility in other applications and fields, e.g., as a therapeutic agent and as an additive for paints, coatings and adhesives and as an antistatic agent for use in photographic and magnetic recording elements.

The polymer useful in the practice of the invention contains units comprising a chelating agent linked to the residue of a poly(amine) moiety in the backbone of the polymer chain with pendent chains of poly(alkylene oxide). The polymer comprises from 2 to 1000 or more, preferably 3 to 1000, of the above described units. In preferred embodiments, the above-described units are recurring units.

In formula (I) above, PAO represents a linear or branched poly(alkylene oxide) moiety. Exemplary poly(alkylene oxide) moieties include poly(ethylene oxides), poly (propylene oxides) and poly(butylene oxides). Preferred poly(alkylene oxides) include poly(ethylene oxides) (PEO), poly(propylene oxides) (PPO) and random and block copolymers of PEO and PPO. PEO containing polymers are particularly preferred when it is desired for the final polymer to possess solubility in water. It is also contemplated that the poly(alkylene oxide) moiety can comprise glycerol poly (alkylene oxide) triethers and linear and block copolymers of alkylene oxides with compatible comonomers such as poly(ethyleneimine-co-ethylene oxide) and grafted block copolymers such as poly(methyl vinyl ether-co-ethylene oxide). For MR imaging applications, preferred poly (alkylene oxide) moieties have an average molecular weight in the range from about 100–20,000, more preferably 250–10,000 daltons. These moieties can be derived from poly(alkylene oxide) moieties which are commercially available in the corresponding diol form and/or can be prepared by techniques well known to those skilled in the art. A particularly preferred class of PEO moieties derived from PEGs can be represented by the structure:

wherein n is 2 to 5,000, preferably 2 to 2500, and more preferably 2 to 500.

The polymer of the invention can comprise the residue of one or more of a wide variety of chelating agents. As is well known, a chelating agent is a compound containing donor atoms that can combine by coordinate bonding with a metal atom to form a cyclic structure called a chelation complex or chelate. This class of compounds is described in the *Kirk-Othmer Encyclopedia of Chemical Technology*, Vol. 5, 339–368.

The residues of suitable chelating agents can be selected from polyphosphates, such as sodium tripolyphosphate and hexametaphosphoric acid;

aminocarboxylic acids, such as ethylenediaminetetraacetic acid, N-(2-hydroxyethyl)ethylenediaminetriacetic acid, nitrilotriacetic acid, N,N-di(2-hydroxyethyl)glycine, ethylenebis(hydroxyphenylglycine) and diethylenetriamine pentacetic acid;

1,3-diketones, such as acetylacetone, trifluoroacetylacetone, and thenoyltrifluoroacetone;

hydroxycarboxylic acids, such as tartaric acid, citric acid, gluconic acid, and 5-sulfosalicylic acid;

polyamines, such as ethylenediamine, diethylenetriamine, triethylenetetramine, and triaminotriethylamine;

aminoalcohols, such as triethanolamine and N-(2-hydroxyethyl)ethylenediamine;

aromatic heterocyclic bases, such as 2,2'-dipyridyl, 2,2'-diimidazole, dipicoline amine and 1,10-phenanthroline;

phenols, such as salicylaldehyde, disulfopyrocatechol, and chromotropic acid;

aminophenols, such as 8-hydroxyquinoline and oxine-sulfonic acid;

oximes, such as dimethylglyoxime and salicylaldoxime;

peptides containing proximal chelating functionality such as polycysteine, polyhistidine, polyaspartic acid, polyglutamic acid, or combinations of such amino acids;

Schiff bases, such as disalicylaldehyde 1,2-propylenediimine;

tetrapyrroles, such as tetraphenylporphin and phthalocyanine;

sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea;

synthetic macrocylic compounds, such as dibenzo[18]crown-6, $(CH_3)_6[14]4,11$-diene$N_4$, and (2.2.2-cryptate); and phosphonic acids, such as nitrilotrimethylenephosphonic acid, ethylenediaminetetra(methylenephosphonic acid), and hydroxyethylidenediphosphonic acid, or combinations of two or more of the above agents.

Preferred residues of chelating agents contain polycarboxylic acid groups and include: ethylenediamine-N, N, N',N'-tetraacetic acid (EDTA); N,N,N',N",N"-diethylenetriaminepentaacetic acid (DTPA); 1,4,7,10-tetraazacyclododecane-N,N',N",N"'-tetraacetic acid (DOTA); 1,4,7,10-tetraazacyclododecane-N,N',N"-triacetic acid (DO3A); 1-oxa-4,7,10-triazacyclododecane-N,N',N"-triacetic acid (OTTA); trans(1,2)-cyclohexanodiethylenetriamine pentaacetic acid (CDTPA)

(B4A)

(P4A)

(TMT)

(DCDTPA)

(PheMT)

Other suitable chelating groups are described in PCT/US91/08253, the disclosure of which is hereby incorporated by reference. In formula I above, Z is the residue of one or more chelating agents. If Z is the residue of multiple chelating units, such units can be linked together by a linking group such as described below.

The residue of the chelating agent is linked to the poly (amine) moiety through chemical bonds between the polyamine nitrogens and the chelator residue.

The R" group of the polyamine may include: hydrogen, alkylene, preferably containing from 1 to 18 carbon atoms such as methylene, ethylene, propylene, butylene and hexylene, such alkylene optionally being interrupted by 1 or more heteroatoms such as oxygen, nitrogen and sulfur or heteroatom-containing groups.

The linking group L may include:
carbon;
nitrogen;

carbonyl;
sulfonyl;
sulfinyl;
ether;
thioether;
ester, i.e., carbonyloxy and oxycarbonyl;
thioester, i.e., carbonylthio and thiocarbonyl;
amide, i.e., iminocarbonyl and carbonylimino;
thioamide, i.e., iminothiocarbonyl and thiocarbonylimino;
thio;
dithio;
phosphate;
phosphonate;
urelene;
thiourelene;
urethane, i.e., iminocarbonyloxy;
thiourethane, i.e., iminothiocarbonylthio;
an amino acid linkage, i.e., a group wherein n=1 and X is H, alkyl, containing from 1 to 18, preferably 1 to 6 carbon atoms, such as methyl, ethyl and propyl, such alkyl optionally being interrupted by 1 or more heteroatoms such as oxygen, nitrogen and sulfur, substituted or unsubstituted aryl, containing from 6 to 18, preferably 6 to 10 carbon atoms such as phenyl, hydroxyiodophenyl, hydroxyphenyl, fluorophenyl and naphthyl, aralkyl, preferably containing from 7 to 12 carbon atoms, such as benzyl, heterocyclyl, preferably containing from 5 to 7 nuclear carbon and one or more heteroatoms such as S, N, P or O, examples of preferred heterocyclyl groups being pyridyl, quinolyl, imidazolyl and thienyl; heterocyclylalkyl, the heterocyclyl and alkyl portions of which preferably are described above; or a peptide linkage, i.e., a group wherein n>1 and each X independently is represented by a group as described for X above. Two or more linking groups can be used, such as, for example, alkyleneimino and iminoalkylene. It is contemplated that other linking groups may be suitable for use herein, such as linking groups commonly used in protein heterobifunctional and homobifunctional conjugation and crosslinking chemistry. Especially preferred linking groups are unsubstituted or substituted imino groups which when linked to the carbonyl in the residue of a chelating agent form an amide.

The linking groups can contain various substituents which do not interfere with the polymerization reaction. The linking groups can also contain substituents which can interfere with the polymerization reaction, but which during the polymerization reaction, are prevented from so doing with suitable protecting groups commonly known in the art and which substituents are regenerated after the polymerization by suitable deprotection. The linking groups can also contain substituents that are introduced after the polymerization. For example, the linking group can be substituted with substituents such as halogen, such as F, Cl, Br or I; an ester group; an amide group; alkyl, preferably containing from 1 to about 18, more preferably, 1 to 4 carbon atoms such as methyl, ethyl, propyl, i-propyl, butyl, and the like; substituted or unsubstituted aryl, preferably containing from 6 to about 20, more preferably 6 to 10 carbon atoms such as phenyl, naphthyl, hydroxyphenyl, iodophenyl, hydroxyiodophenyl, fluorophenyl and methoxyphenyl; substituted or unsubstituted aralkyl, preferably containing from 7 to about 12 carbon atoms, such as benzyl and phenylethyl; alkoxy, the alkyl portion of which preferably contains from 1 to 18 carbon atoms as described for alkyl above; alkoxyaralkyl, such as ethoxybenzyl; substituted or unsubstituted heterocyclyl, preferably containing from 5 to 7 nuclear carbon and heteroatoms such as S, N, P or O, examples of preferred heterocyclyl groups being pyridyl, quinolyl, imidazolyl and thienyl; a carboxyl group; a carboxyalkyl group, the alkyl portion of which preferably contains from 1 to 8 carbon atoms; the residue of a chelating group, preferably such as described for Z above; or a poly(alkylene oxide) moiety, preferably such as described for Q above.

The metal content in the polymer can vary from about 0.1 up to about 30% based on the total weight of the polymer. For MR imaging, the polymer preferably contains the paramagnetic metal in an amount of from 1 to 25%, more preferably 2–20% by weight.

For MR imaging, the polymer preferably comprises from 2 to about 500, more preferably 5 to 100 recurring units. If the polymer contains a peptide that can be hydrolyzed, then the polymer can contain from 1 to several hundred paramagnetic metal ions per molecule.

The polymer in structure (I) can be capped at the termini with groups independently selected from Z or hydrogen. In preferred embodiments, wherein the polymer is a polyamide, the polymer can be capped with groups such as hydrogen or hydroxyl groups or with groups derived from polyamide chain terminating agents such as monoamines and monoacyl derivatives such as monoanhydrides, e.g., acetic anhydride, or with groups derived from the residue of a chelating group as defined above. It is further contemplated that cyclic polymers, i.e., non-capped polymers can be prepared.

The polymer of this invention can be prepared in water-soluble, water-dispersible or water-insoluble forms depending upon the intended application. The polymer can be crosslinked or non-crosslinked. The molecular weight of the polymer can vary widely, i.e., from about 1,000 to $10^8$ or greater, as measured by gel permeation chromatography (GPC). The water-soluble polymer preferably is of molecular weight from 1,000 to about 250,000. For MR imaging, the polymer preferably is of molecular weight 5,000–$10^6$, more preferably 10,000–100,000.

The polymer of this invention can be prepared by contacting a reactive poly(alkylene oxide) species with a chelating agent or precursor thereof containing reactive functionality in a non-reactive solvent to form the polymer. The poly(alkylene oxide) can be substituted or unsubstituted.

The preferred reaction conditions, e.g., temperature, pressure, solvent, etc., depend primarily on the particular reactants selected and can be readily determined by one skilled in the art.

Suitable reactive poly(alkylene oxide) species include α-(polyamino)-poly(alkylene oxides), α-(polyhydrazino)-poly(alkylene oxides), α-(polyisocyanato)-poly(alkylene oxides), α-(polyhydroxy)-poly(alkylene oxides), α-poly(aldehydic)-poly(alkylene oxides), α-(polycarboxy)-poly(alkylene oxides), α-(poly[vinyl sulphonyl]-poly(alkylene oxides), α-(polyphosphato)-poly(alkylene oxides), α-(poly-[N,N-dialkylaminophosphoramidato]-poly(alkylene oxides), α-(polyoxirano)-poly(alkylene oxides), α-(polyalkoxy)-poly(alkylene oxides), α-(polysulphonato)-poly(alkylene oxides), and the like. The above-described poly(alkylene oxide) species are linear polymers containing multi-functionality at one end of the polymer and no reactive functionality at the opposite end; branched poly(alkylene oxide) species relating to the above containing multi-functionality at one end of the polymer only are also useful.

Suitable chelating agents and precursors thereof containing reactive functionality include polycarboxylic acids in dianhydride form, di(sulfonyl chlorides), di(alkyl sulfates), di(vinyl sulfones), and the like. As will be recognized by one skilled in the art, a suitably blocked pregenitor to the chelating agent or precursor thereof containing reactive functionality can be contacted with the reactive poly(alkylene oxide) moiety to form the polymer, and then the blocking group can be subsequently removed by techniques known in the art. It is contemplated that additional chelating functional groups can be introduced by suitable chemical modification at the unblocked sites. If hydroxy substituents are to be selectively present in the final polymer, they must be temporarily blocked during polymerization, e.g., by conventional blocking techniques to minimize formation of undesirable byproducts, e. g., polyesteramide derived therefrom. However, for some purposes, polyesterpolyamides which contain one or more ester linking groups in the backbone of the polymer are contemplated to be useful.

In a preferred embodiment, the polymer of this invention can be prepared by reacting a linear α-(polyamino)-poly(alkylene oxide) with a precursor of a chelating agent in an internal dianhydride form.

The α-(polyamino)-poly(alkylene oxide) can be prepared by reacting an activated form of the poly(alkylene oxide) with a polyamine. The polyamino group can be introduced by other methods known in the art. Suitable illustrative polyamines include diaminohexane, tris(aminoethyl)amine, and diethylenetriamine.

The linear poly(alkylene oxide) in its α-hydroxy-ω-methoxy form is widely available commercially or can be prepared by techniques well known to those skilled in the art. The poly(alkylene oxide) is activated for nucleophilic displacement by reacting it with an activator such as p-toluenesulfonyl chloride, thionyl chloride, thionyl bromide, an alkylsulfonyl chloride, e.g., $CH_3SO_2Cl$, a sulfonic acid anhydride, or any other suitable activator known in the art. The activated form of the poly(alkylene oxide) thus can be a tosylate, a chloride, a bromide, etc.

The activated form of the poly(alkylene oxide) is reacted preferably with a stoichiometric excess of the polyamine, in an inert solvent preferably at a temperature, e.g., 100–160° C., and pressure, e.g., 1 to 10 atmospheres, sufficient to drive the reaction to completion. Suitable solvents include dioxane, ethanol, and other alcohols. Thereafter, the α-(polyamino)-poly(alkylene oxide) preferably is isolated, e.g., by evaporation or precipitation, and purified, e.g., by dissolving in a suitable solvent such as methylene chloride, chloroform or trichloroethane, and then washing the solution with an excess of aqueous NaOH, or by any other suitable isolation and purification techniques.

The internal anhydride forms of the chelating agents described above are commercially available and/or can be prepared by techniques known in the art. For example, the internal anhydride forms of EDTA and DTPA are commercially available. The internal anhydride forms of B4A, P4A and TMT can be prepared by techniques known in the art. For example, the anhydrides can be prepared by heating the corresponding acids in acetic anhydride in the presence of pyridine as catalyst. Methods for the preparation of B4A, P4A and TMT are described in U.S. Pat. No. 4,859,777. Mixed anhydrides are also suitable.

The reactive α-(polyamino)-poly(alkylene oxide) can be reacted with the internal dianhydride in a non-reactive solvent to form the unmetallized polymer. The reaction conveniently can take place at approximately room temperature and atmospheric pressure. However, higher and lower temperatures and pressures are contemplated. Suitable solvents include dimethylsulfoxide, dimethylformamide, acetonitrile, chloroform, dichloromethane and 1,2-dichloroethane. The nonmetallized polymer preferably is isolated and then purified, e.g., by diafiltration.

The metallized polymer can be formed by contacting the unmetallized polymer with a source of metal ions. This can be conveniently accomplished by adding a solution of or a solid salt or oxide of the metal to a solution, preferably an aqueous solution, of the polymer. Thereafter, the chelated polymer preferably is diafiltered in water to remove excess unchelated metal.

A general reaction scheme for this method of preparing the polymers of this invention and illustrative examples are set forth below.

Alternatively, the polymer can be prepared in a condensation polymerization reaction between a suitable polyamine and a diacid containing the metallized chelating group, in a suitably activated form, e.g., in the form of an activated diester.

The molecular weight of the polymer product depends upon many factors including, for example, the molecular weight of the starting poly(alkylene oxide) moiety, the presence or absence of reactive polymerization chain terminating agents such as monoanhydrides or monoamines in the case of polyamides which reduce molecular weight by end-capping the polymer during the polymerization process, the presence or absence of reactive crosslinkers which increase the molecular weight of the polymer during polymerization, and the relative concentrations of the poly(alkylene oxide) and chelator present during the polymerization reaction which in turn affects the number of recurring units in the polymer product. The preparation of insoluble and water-soluble polymers of molecular weight 1,000 to $10^8$ can be accomplished by routine experimentation by one skilled in the art of polymer synthesis techniques.

The polymer preferably is prepared in a water soluble, i.e., injectable form when used as an MR contrast agent for blood pool imaging or as a composition intended to be administered intravenously. On the other hand, the polymer can be prepared preferably as a water-insoluble polymer when intended to be administered orally as an MR contrast agent for gastro-intestinal imaging.

The dosages of the contrast agent used according to the method of the present invention will vary according to the precise nature of the contrast agent used. Preferably however, the dosage should be kept as low as is consistent with achieving contrast enhanced imaging and volumes minimized for IV drip or bolus injection. In this way, the toxicity potential is minimized. For most MR contrast agents the appropriate dosage will generally range from 0.02 to 3 mmol paramagnetic metal/kg body weight, especially 0.05 to 1.5 mmol/kg, particularly 0.08 to 0.5, more especially 0.1 to 0.4 mmol/kg. It is well within the skill of the average practitioner in this field to determine the optimum dosage for any particular MR contrast agent by relatively routine experimentation, for both in vivo or in vitro applications.

Contrast agents may be formulated with conventional pharmaceutical or veterinary aids, for example stabilizers, antioxidants, osmolality adjusting agents, buffers, pH adjusting agents, etc., and may be in a form suitable for injection or infusion directly or after dispersion in or dilution with a physiologically acceptable carrier medium, e.g., water for injection. Thus the contrast agents may be formulated in conventional administration forms such as powders, solutions, suspensions, dispersions, etc., however solutions, suspensions and dispersions in physiologically acceptable carrier media will generally be preferred.

The contrast agents may be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Parenterally administrable forms, e.g., intravenous solutions, should of course be sterile and free from physiologically unacceptable agents, and should have low osmolality to minimize irritation or other adverse effects upon administration and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the contrast agents and which will not interfere with the manufacture, storage or use of products.

The following examples further illustrate the invention.

Examples 1–4 describe the preparation of a cross-linked polymer (Ia) prepared from methoxypolyethylene glycol of average MW 2000 in which:

L and R"=N(CH$_2$CH$_2$NH$_2$)$_3$
R=CH$_3$
PAO=Polyethylene glycol
metal=Gd(III)
chelator=DTPA
y=1
x=4.2 (average)

Examples 5–8 and 9–12 describe analogous cross-linked polymers (Ib and Ic respectively) prepared from methoxypolyethylene glycols of average MW 750 and 550, respectively, wherein:

L and R"=N(CH$_2$CH$_2$NH$_2$)$_3$
R=CH$_3$
PAO=Polyethylene glycol
metal=Gd(III)
chelator=DTPA
y=1
x=11.7 (average) and 9.3 (average), respectively

Examples 13–15 describe a linear polymer (Id) in which:

L and R"=H$_2$NCH$_2$CH$_2$(OCH$_2$CH$_2$)$_2$NH$_2$
R=CH$_3$
PAO=Polyethylene glycol
metal=Gd(III)
chelator=DTPA
y=0
x=3.3 (average)

Polymers Ia, Ib and Ic were prepared as illustrated in scheme 1:

Scheme 1:

n = 1 to 5,000

Polymer Id was prepared as illustrated in scheme 2:

n = 1 to 5,000

EXAMPLE 1

A solution of methoxy-PEG of average MW 2000 (44.20 g, 22.1 mmol; Union Carbide) in 663 ml of toluene was refluxed with azeotropic removal of water for several hours. The cooled toluene solution was treated with triethylamine (7.39 ml, 53.0 mmol), 4-dimethylaminopyridine (0.270 g, 2.21 mmol) and tosyl chloride (9.27 g, 48.6 mmol) and heated in an oil bath at 60° C. for 48 hours. An additional 3.70 ml of triethylamine, 0.135 g of dimethylaminopyridine and 4.64 g of tosyl chloride was added and heating continued at 60° C. for 144 hours. An additional 3.70 ml of triethylamine, 0.135 g of dimethylaminopyridine and 4.64 g of tosyl chloride was added and heating continued at 60° C. for another 144 hours. The reaction mixture was then cooled and filtered. The filtrate was extracted three times with water. The combined aqueous extracts were washed three times with ether, then extracted three times with chloroform. The chloroform extracts were dried over anhydrous $MgSO_4$ and concentrated to 40.65 g (85%) of product 1a.

EXAMPLE 2

A solution of 24.87 g (11.55 mmol) of 1a in 250 mls of absolute EtOH was treated with 17.3 ml (115 mmol) of tris(2-aminoethyl)amine. The reaction mixture was heated in a stainless steel bomb at 160° C. for 16 hours. The solvent was removed by evaporation and the residue dissolved in 500 ml of water and made basic with 23 ml of 1 N NaOH. The basic solution was washed twice with ether, then extracted with chloroform. The chloroform extracts were dried over anhydrous $MgSO_4$; solvent evaporation followed by heating at 90° C. under vacuum(1 mm) to remove residual tris(2-aminoethyl)amine yielded 23.94 g (97%) of 2a.

EXAMPLE 3

A solution of 3.99 g (1.88 mmol) of 2a in 40 mls of acetonitrile was treated with triethylamine (0.784 ml, 5.62 mmol) and diethylenetriaminepentaacetic acid dianhydride (1.005 g, 2.81 mmol). After 3.25 hours at room temperature acetic anhydride 0.18 ml (1.9 mmol) was added and stirring continued for an additional 30 min., then 160 ml of water was added.

EXAMPLE 4

The solution of crude polymer 3a from Example 3 was treated with gadolinium(III) chloride hexahydrate (1.15 g, 3.09 mmol) then diafiltered against water in a diafiltration cell equipped with a 10,000 MW cut-off membrane. The pH of the solution was adjusted to 7 with NaOH then the solution was filtered through a 0.2 mm nylon filter. Lyophilization yielded 2.81 g of product (Ia) of average molecular weight 12,100 daltons as determined by SEC-HPLC using PEG molecular weight standards; 7.60% gadolinium by weight.

Intravenous administration of 100, 300 and 1000 mmol Gd/Kg of a 100 mM Gd solution of Ia in isotonic saline to mice resulted in no deaths and no abnormalities upon necropsy after 7 days.

EXAMPLE 5

A solution of methoxy-PEG of average MW 750 (100.0 g, 0.1333 mol; Sigma Chemical Co.) in 1500 ml of toluene was refluxed with azeotropic removal of water for several hours. The cooled toluene solution was treated with triethylamine (61.3 ml, 0.440 mol), 4-dimethylaminopyridine (1.62 g, 0.0133 mol) and tosyl chloride (76.26 g, 0.400 mol) and heated in an oil bath at 60° C. for 48 hours. The cooled reaction mixture was work up as described in Example 1 to yield 100.4 g (83%) of product 1b.

EXAMPLE 6

Product 1b from Example 5 was reacted with tris(2-aminoethyl)amine as described in Example 2 to give a 97% yield of 2b.

EXAMPLE 7

A solution of 5.39 g (6.14 mmol) of 2b in 54 mls of acetonitrile was treated with triethylamine (2.57 ml, 18.4 mmol) and diethylenetriaminepentaacetic acid dianhydride (3.29 g, 9.20 mmol). After 1.0 hour at room temperature 216 mls of water was added and the solution stirred for 30 min.

EXAMPLE 8

The solution of crude polymer 3b from Example 7 was treated with gadolinium(III) chloride hexahydrate (3.76 g, 10.1 mmol) then diafiltered against water in a diafiltration cell equipped with a 10,000 MW cut-off membrane. The pH of the solution was adjusted to 7 with NaOH then the solution was filtered through a 0.2 mm nylon filter. Lyophilization yielded 6.05 g of product (Ib) of average molecular weight 19,100 daltons as determined by SEC-HPLC using PEG molecular weight standards; 13.1% gadolinium by weight.

Intravenous administration of 100, 300 and 1000 mmol Gd/Kg of a 100 mM Gd solution of Ib in isotonic saline to mice resulted in no deaths, no clinical signs and no abnormalities upon necropsy after 7 days.

EXAMPLE 9

A solution of methoxy-PEG of average MW 550 (66.67 g, 0.1212 mol; Sigma Chemical Co.) in 1000 ml of toluene was refluxed with azeotropic removal of water for several hours. The cooled toluene solution was treated with triethylamine (55.75 ml, 0.4000 mol), 4-dimethylaminopyridine (2.96 g, 0.0242 mol) and tosyl chloride (69.33 g, 0.3636 mol) and heated in an oil bath at 60° C. for 48 hours. The cooled reaction mixture was work up as described in Example 1 to yield 47.58 g (56%) of product 1c.

EXAMPLE 10

Product 1c from Example 9 was reacted with tris(2-aminoethyl)amine as described in Example 2 to give a 84% yield of 2c.

EXAMPLE 11

A solution of 4.23 g (6.24 mmol) of 2c in 42 mls of acetonitrile was treated with triethylamine (2.61 ml, 18.7 mmol) and diethylenetriaminepentaacetic acid dianhydride (3.34 g, 9.36 mmol). After 1.0 hour at room temperature 168 mls of water was added and the solution stirred for 30 min.

EXAMPLE 12

The solution of crude polymer 3c from Example 11 was treated with gadolinium(III) chloride hexahydrate (3.65 g, 9.83 mmol) then diafiltered against water in a diafiltration cell equipped with a 10,000 MW cut-off membrane. The pH of the solution was adjusted to 7 with NaOH then the solution was filtered through a 0.2 mm nylon filter. Lyophilization yielded 4.15 g of product (Ic) of average molecular weight 13,600 daltons as determined by SEC-HPLC using PEG molecular weight standards; 15.6% gadolinium by weight.

Intravenous administration of 100, 300 and 1000 mmol Gd/Kg of a 100 mM Gd solution of Ic in isotonic saline to mice resulted in no deaths, no clinical signs and no abnormalities upon necropsy after 7 days.

EXAMPLE 13

Product 1a from Example 1 was reacted with "ED-148" as described in Example 2 to give 4 in 75% yield after precipitation of a methylene chloride solution with ether.

EXAMPLE 14

A solution of 1.45 g (0.680 mmol) of 4 in 14.5 mls of acetonitrile was treated with triethylamine (0.190 ml, 1.36 mmol) and diethylenetriaminepentaacetic acid dianhydride (0.267 g, 0.748 mmol). After 4 hours at room temperature 58 mls of water was added.

EXAMPLE 15

The solution of crude polymer 5 from Example 14 was treated with gadolinium(III) chloride hexahydrate (0.215 g, 0.578 mmol) then diafiltered against water in a diafiltration cell equipped with a 5,000 MW cut-off membrane. The solution was filtered through a 0.45 mm nylon filter and lyophilized to yield 1.06 g of product (Id) of average molecular weight 8,700 daltons as determined by SEC-HPLC using PEG molecular weight standards.

Viscosity Measurements. Viscosities of aqueous solutions of Ia (Example 4), Ib (Example 8), Ic (Example 12) and a linear copolymer of similar molecular weight prepared from polyethylene glycol(1450)-diamine and DTPA [PEG(1450)-DTPA(Gd)] are shown in Table 1. The compound is disclosed in PCT/US93/09766. The viscosities were measured with a Brookfield viscometer (Model LVCP DVII-plus) equipped with a cone and plate spindle and a jacketed sample cell for temperature control. The temperature was controlled with a LAUDA RM6 circulating water bath. The viscometer was calibrated using Brookfield viscosity standards that ranged from 5–100 cP

TABLE 1

Polymeric Gd-Chelate Viscosities

| Polymer | Concentration | | Viscosity |
|---|---|---|---|
| | mg Polymer/ml | mM Gd | cP @ (° C.) |
| Ia (Example 4) | 210. | 100. | 13.5 (20° C.) |
| Ib (Example 8) | 120. | 100. | 5.3 (20° C.) |
| Ic (Example 12) | 100. | 100. | 2.2 (25° C.) |
| | 149. | 147. | 3.3 (25° C.) |
| | 199. | 196. | 5.1 (25° C.) |
| PEG (1450)-DTPA (Gd) | 104. | 46.0 | 9.1 (20° C.) |
| | 120. | 53.1 | 11.6 (20° C.) |
| | 210. | 92.9 | 45.3 (20° C.) |
| | 226. | 100.0 | 56.1 (20° C.) |

The data shows that the compositions of this invention produce solutions of very low viscosity. For example, the viscosities of 100 mM Gd solutions of Ia (13.5 cP), Ib (5.3 cP) and Ic (2.2 cP) are much lower than a 100 mM solution of polymeric PEG(1450)-DTPA(Gd) (56.1 cP). The compositions of this invention are also significantly less viscous than polymeric PEG(1450)-DTPA(Gd) when compared at equal mg polymer/ml concentrations: 13.5 cP for Ia vs. 45.3 cP for polymeric PEG(1450)-DTPA(Gd) at 210 mg polymer/ml and 5.3 cP for Ib vs. 11.6 cP for polymeric PEG(1450)-DTPA(Gd) at 120 mg polymer/ml.

Figure 1:
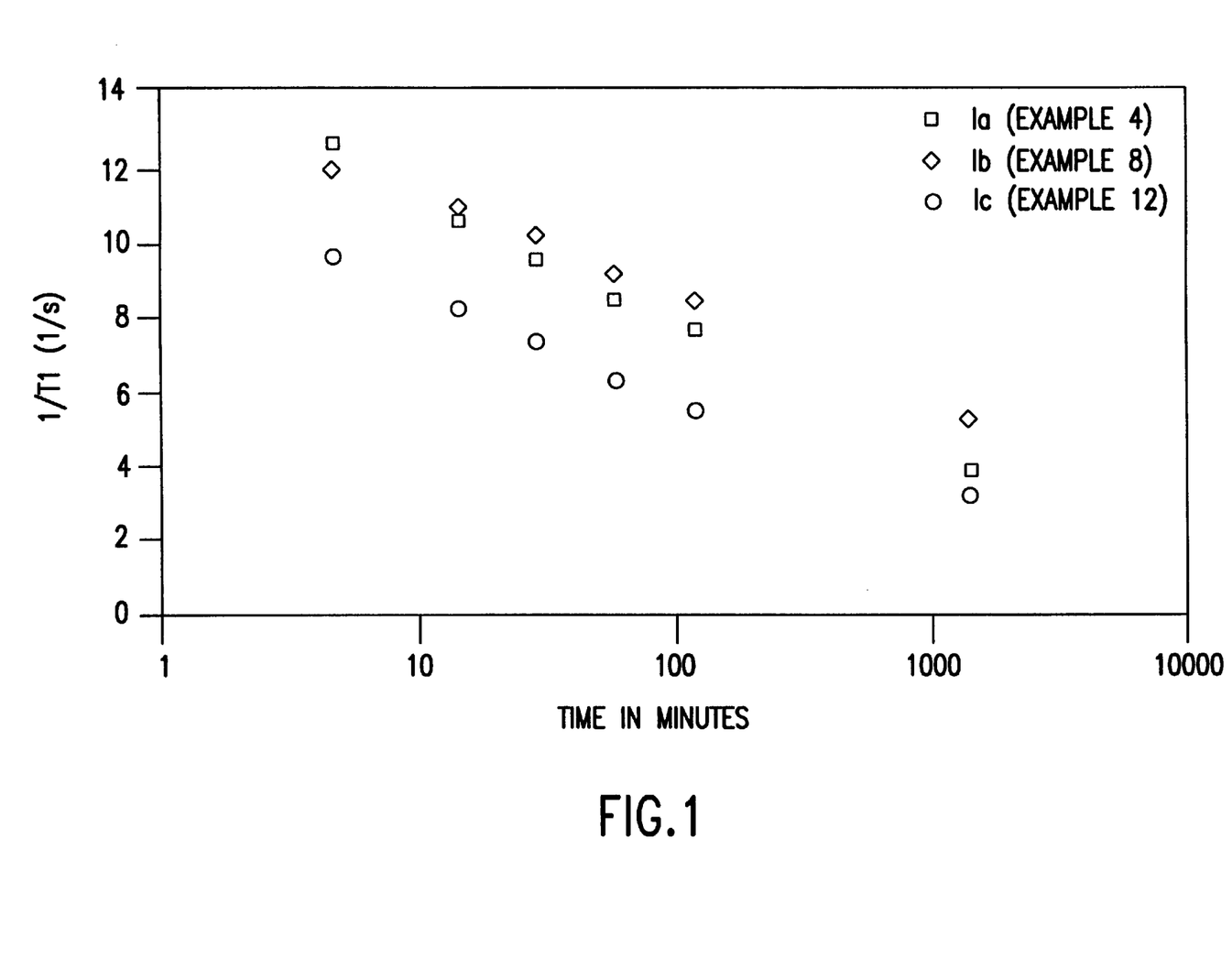
FIG. 1 is a plot of rabbit blood 1/T1 over time following intravenous administration of various compositions of this invention.

Determination of Blood Pool Retention in Rabbits. Rabbits were prepared with surgically implanted percutaneous catheters in the lateral ear vein. Formulations of polymers Ia (Example 4), Ib (Example 8) and Ic (Example 12) containing 100 mM Gd in isotonic saline were injected into the opposite ear of the rabbit at a dose of 0.06 mmol Gd/Kg. Blood samples were withdrawn through the catheter and collected in heparin tubes at 0, 5, 15, 30, 60 minutes, 2 hours and 24 hours following the injection. $T_1$ measurements were made on the blood samples using a Bruker Mini-Spec operating at 20 MHz and 40° C. The data is presented graphically in FIG. 1.

The data shows that administering the compositions of this invention to rabbits results in significant increases in blood $1/T_1$ for at least 120 minutes. Prolonged blood $1/T_1$ enhancement makes these agents useful for vascular imaging as exemplified in FIGS. 3 and 4.

Figure 2:
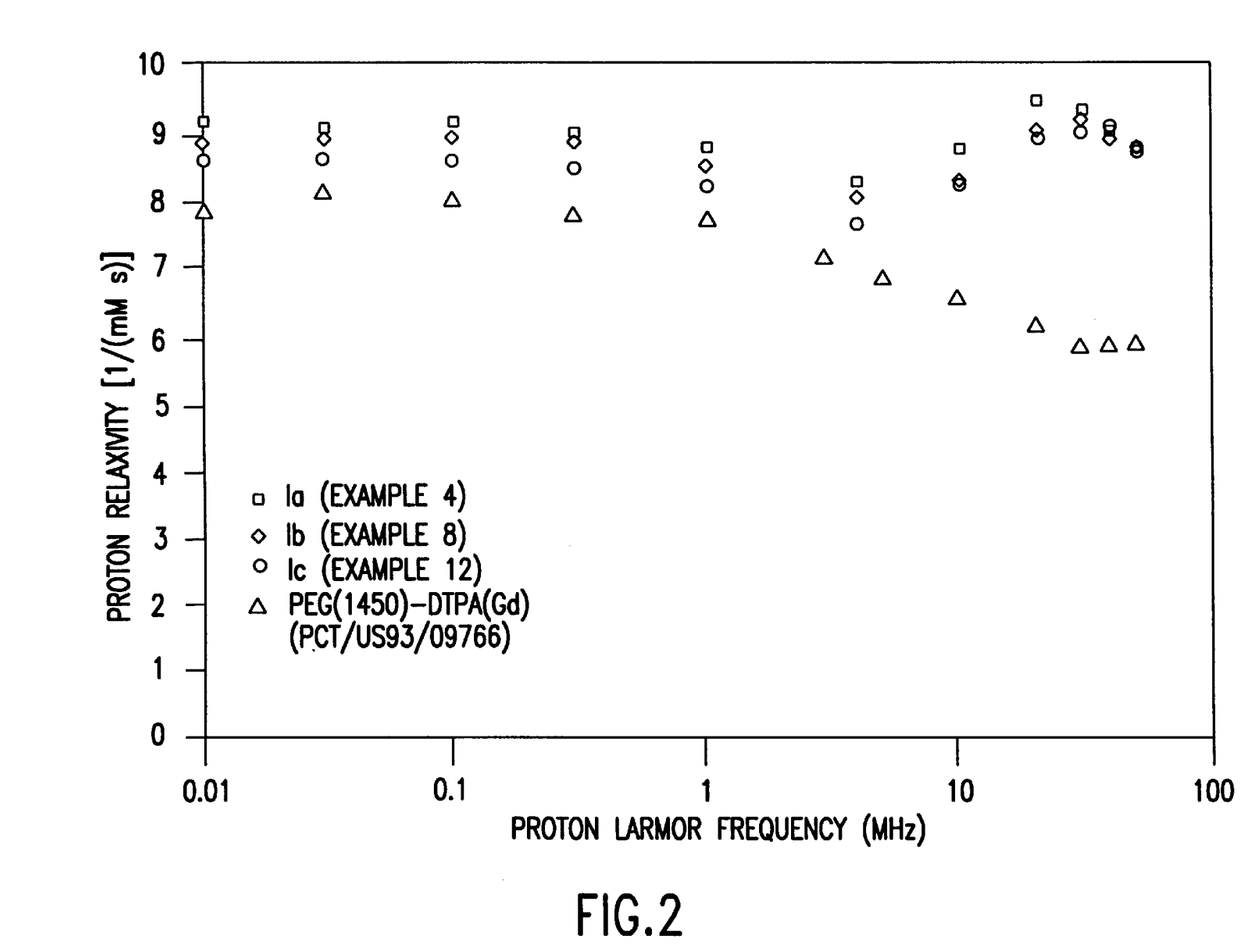
FIG. 2 is a plot of proton relaxivity versus proton larmor frequency for various compositions of this invention and a comparative composition.

Nuclear Magnetic Resonance Dispersion Curves. NMRD curves were obtained for polymers Ia (Example 4), Ib (Example 8) and Ic (Example 12) at 35° C. The data is presented graphically in FIG. 2 along with comparative data for polymeric PEG(1450)-DTPA(Gd), a compound disclosed in PCT/US93/09766. The results demonstrate the improved relaxivities of the compositions of this invention in comparison with the linear polymer PEG(1450)-DTPA (Gd). The improvement in relaxivity is particularly noteworthy at proton Larmor frequencies in the 20 to 60 MHz range, corresponding to the commonly employed clinical magnet field strengths of 0.5–1.5 Tesla.

MR IMAGING STUDIES

The composition of Example 12, polymeric PEG(1450)-DTPA(Gd) (a comparative compound of similar molecular weight disclosed in PCT/US93/09766) and Magnevist® (a commercial non-polymeric comparison) were imaged in normal male New Zealand White Rabbits (3 rabbits/dose) employing 3D-TOF MR angiography of the abdominal vasculature at 1.5T (GE Signa, Milwaukee, Wis.) pre- and post-contrast administration. Imaging parameters were: Field of view (FOV)=24 cm, axial aquisition, Repetition time (TR)=33, 3 mm slice thickness, 60 partitions, 256×256 matrix, and 1 excitation (1 NEX). At 5 minutes post injection, MRA was performed with the above parameters and a 30° flip angle; immediately following this sequence (15 minutes post injection), MRA was performed with the same parameters and a 90° flip angle. Region-of-interest (ROI) measurements were performed of the high (intrahepatic) and mid inferior vena cava (IVC) and of paraspinal musculature on both pre- and post-contrast sequences. Three ROI measurements were performed at both IVC levels and averaged to yield a single value. Percent contrast with background was computed as $(SI_{IVC}-SI_{muscle})/SI_{muscle}\times 100$ (SI=signal intensity). The results are shown graphically in FIGS. 3 and 4.

Figure 3:
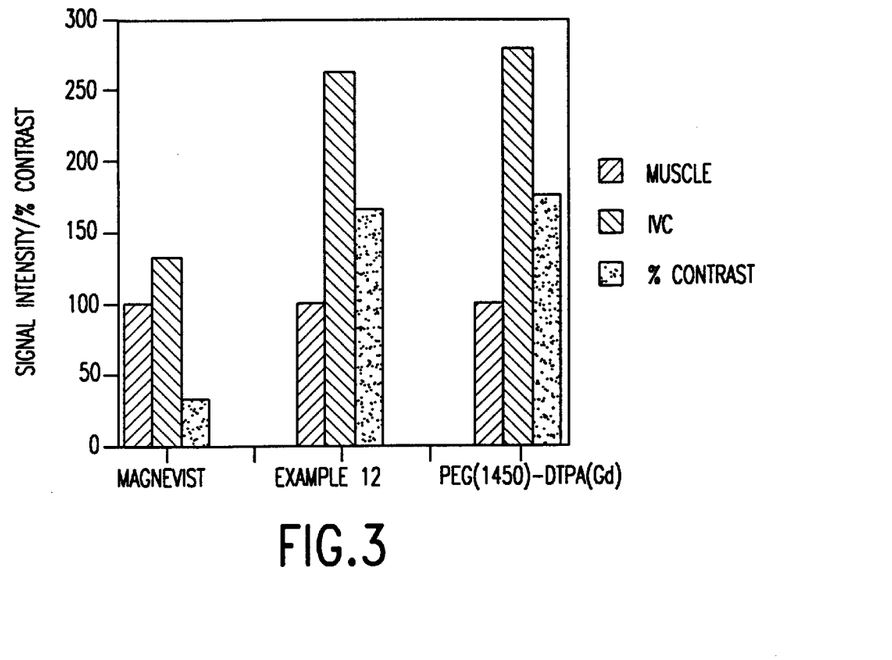
FIGS. 3 and 4 show the results of an MR imaging experiment with one composition of this invention and two comparative agents.
Figure 4:
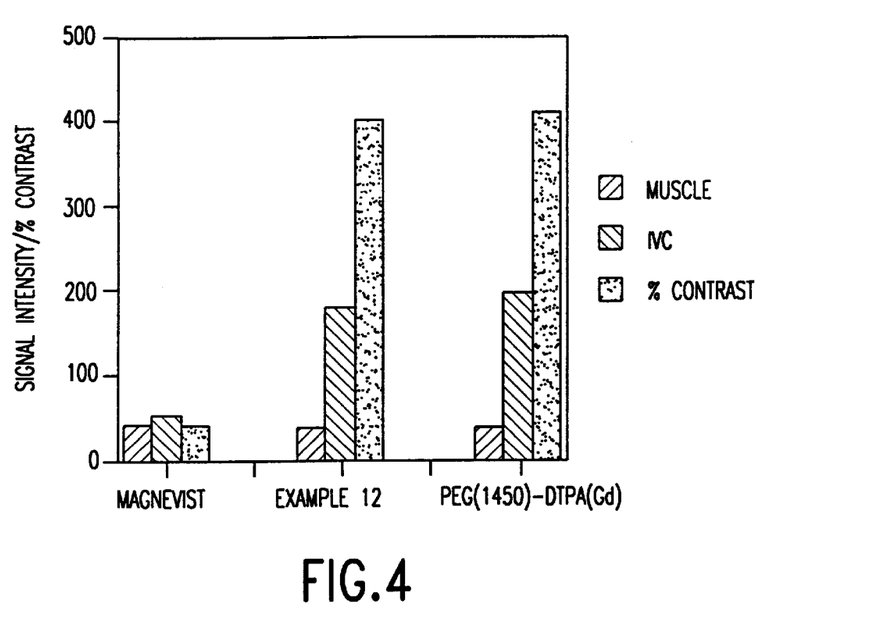

As indicated by the graphs in FIGS. 3 and 4, the representative composition of this invention exhibits outstanding enhancement of the vasculature particularly in comparison with the low molecular weight agent Magnevist®. In addition, % Contrast (high (intrahepatic) and mid inferior vena cava (IVC) versus paraspinal musculature) is comparable to the linear polymer PEG(1450)-DTPA(Gd) at lower dose (0.056 mmol Gd/Kg vs. 0.08 mmol Gd/Kg).

The invention has been described in detail with particular reference to certain preferred embodiments thereof, but it will be understood that variations and modifications can be effected within the spirit and scope of the invention.

I claim:

1. A polymer comprising polymer repeating units of formula (I):

(I)

wherein

R=H or an alkyl group;

R'=H, alkyl, aralkyl or —PAO—OR;

PAO=a polyalkylene oxide of MW 200–20,000;

metal=a paramagnetic or radioactive metal;

chelator=the residue of a chelating agent.;

y–1–10;

x=2–1000;

L=a carbon, amino, imido, nitrilo, imino, alkylene, carbonyl, sulfonyl, sulfinyl, ether, thioether, ester, thioester, amide, thioamide, thio, dithio, phosphate, phosphonate, urelene, thiourelene, urethane, thiourethane, an amino acid linkage, or a peptide linkage; and R"=a bond or an alkylene group optionally interrupted by one or more nitrogen or sulfur heteroatoms.

2. The polymer of claim 1 wherein the metal ion is selected from the group consisting of $Gd^{+3}$, $Fe^{+3}$, $Mn^{+2}$, $Mn^{+3}$, $Dy^{+3}$, and $Cr^{+3}$.

3. The polymer of claim 1 wherein the residue of the chelating agent is selected from the group consisting of EDTA, DTPA, DOTA, DO3A, OTTA, CDTPA, P4A, B4A, PheMT, DCDTPA and TMT.

4. The polymer of claim 1 wherein L provides an imino or nitrilo linkage.

5. The polymer of claim 1 wherein PAO— is selected from the group consisting of a poly(ethylene oxide) moiety, a poly(propylene oxide) moiety and a poly ethylene oxide)-co-poly(propylene oxide) moiety.

6. The polymer of claim 1 wherein —OR is selected from the group consisting of OH, $OCH_3$, $O(CH_2)_pCH_3$ where p=2 to 20.

7. The polymer of claim 1 comprising from 5 to 100 of said units.

8. The polymer of claim 1 wherein the metal is $Gd^{+3}$ or $Dy^{+3}$; $LR"_3$ is $N(CH_2CH_2)_3$ or $CH_2CH_2(OCH_2CH_2)_2$; R is $CH_3$; R' is H or —PAO—OR; PAO is a poly(ethylene oxide) moiety of MW 200–20,000; and the chelator is DTPA.

9. The polymer of claim 1 wherein the metal is $Gd^{+3}$; $LR"_3$ is $N(CH_2CH_2)_3$; R is $CH_3$; R' is H; PAO is poly (ethylene oxide) moiety of MW 550; and the chelator is DTPA.

10. A method of performing a magnetic resonance diagnostic procedure in a human or non-human body comprising administering to the body a contrast enhancing amount of the polymer of claim 1 and then exposing the body to a magnetic resonance measurement step to image at least a portion of the body.

11. The method of claim 8 wherein the polymer is administered with a pharmaceutically acceptable carrier.

12. A polymer as claimed in claim 1 in which the linking group $LR"_3$ is $N(CH_2CH_2)_3$, $N(CH_2CH_2)_2(CH_2CH_2NH_2)$ or $CH_2CH_2(OCH_2CH_2)_2$.

* * * * *